US012576007B2

(12) United States Patent
Bellini et al.

(10) Patent No.: US 12,576,007 B2
(45) Date of Patent: Mar. 17, 2026

(54) FLEXIBLE BAG FOR THE PREPARATION OF ADIPOSE TISSUE GRAFTS AND RELATIVE KIT

(71) Applicant: BIOPSYBELL S.R.L, Mirandola (IT)

(72) Inventors: Tiziana Bellini, Mirandola (IT); Carlo Ricca Prandi Bellini, Mirandola (IT)

(73) Assignee: BIOPSYBELL S.R.L., Mirandola (IT)

( * ) Notice: Subject to any disclaimer, the term of this patent is extended or adjusted under 35 U.S.C. 154(b) by 24 days.

(21) Appl. No.: 18/010,628

(22) PCT Filed: Jun. 18, 2021

(86) PCT No.: PCT/IB2021/055404
§ 371 (c)(1),
(2) Date: Dec. 15, 2022

(87) PCT Pub. No.: WO2021/255706
PCT Pub. Date: Dec. 23, 2021

(65) Prior Publication Data
US 2023/0225941 A1      Jul. 20, 2023

(30) Foreign Application Priority Data

Jun. 19, 2020      (IT) ........................ 102020000014728

(51) Int. Cl.
*A61J 1/14*          (2023.01)
*A61M 1/00*          (2006.01)
(Continued)

(52) U.S. Cl.
CPC .................. *A61J 1/14* (2013.01); *A61M 1/69* (2021.05); *A61M 1/895* (2021.05); *B01D 29/27* (2013.01);
(Continued)

(58) Field of Classification Search
CPC .. A61M 1/895; A61M 1/893; A61M 2202/08; A61M 2202/005;
(Continued)

(56) References Cited

U.S. PATENT DOCUMENTS 5,695,489 A * 12/1997 Japuntich ............ A61M 1/3636
604/408
5,772,644 A * 6/1998 Bark ...................... A61M 1/79
600/580
(Continued)

FOREIGN PATENT DOCUMENTS

CN          207659440 U      7/2018
WO      WO-0224256 A1 *  3/2002  .......... A61M 1/0218
(Continued)

OTHER PUBLICATIONS

International Search Report and Written Opinion for Corresponding International Application No. PCT/IB2021/055404 dated Oct. 14, 2021.

*Primary Examiner* — Andrew J Mensh
*Assistant Examiner* — Arjuna P Chatrathi
(74) *Attorney, Agent, or Firm* — LUCAS & MERCANTI, LLP

(57) ABSTRACT

A flexible bag for the preparation of an adipose tissue graft provided with a proximal end and a distal end and comprising: a front wall and a rear wall, which are connected to one another to define a receiving space on the inside; a first filter arranged inside the bag to divide the receiving space into a first chamber and a second chamber and to micro-fragment the adipose tissue to obtain a micro-fragmented adipose tissue; and a second filter arranged inside the second chamber to obtain a third chamber and to obtain the graft by separating a waste material from the micro-fragmented adipose tissue. The first filter comprises a distal edge which is connected to the front wall between the proximal end and the distal end and the second filter comprises a proximal edge which is connected to the rear wall between the proximal end and the distal end.

20 Claims, 4 Drawing Sheets

(51) Int. Cl.
  *B01D 29/27*         (2006.01)
  *B01D 29/56*         (2006.01)
(52) U.S. Cl.
  CPC ......... *B01D 29/56* (2013.01); *A61M 2202/08*
       (2013.01); *A61M 2205/75* (2013.01); *B01D*
       *2201/188* (2013.01); *B01D 2201/605*
       (2013.01); *B01D 2201/607* (2013.01)
(58) Field of Classification Search
  CPC .. A61M 2202/0042; A61M 2205/7545; A61M
                             2205/75
  See application file for complete search history.

(56)                References Cited

U.S. PATENT DOCUMENTS

| | | | | |
|---|---|---|---|---|
| 5,792,133 | A * | 8/1998 | Rochat .................. | A61M 1/604 |
| | | | | 604/408 |
| 5,941,866 | A * | 8/1999 | Niedospial, Jr. ...... | A61J 1/1412 |
| | | | | 604/408 |
| 6,316,247 | B1 * | 11/2001 | Katz ................... | A61L 27/3604 |
| | | | | 435/308.1 |
| 8,309,342 | B2 * | 11/2012 | Stubbers .............. | C12N 5/0653 |
| | | | | 435/267 |
| 8,857,327 | B2 * | 10/2014 | Stefani ..................... | B30B 5/04 |
| | | | | 425/408 |
| 8,857,627 | B2 * | 10/2014 | Yokomizo ........... | A61M 1/3636 |
| | | | | 210/450 |
| 9,192,939 | B2 * | 11/2015 | Tremolada ............. | C12M 45/02 |
| 2010/0279405 | A1 * | 11/2010 | Peterson .............. | C12N 5/0653 |
| | | | | 435/297.1 |
| 2014/0276384 | A1 * | 9/2014 | Schwab .................. | A61M 5/20 |
| | | | | 604/82 |
| 2015/0374888 | A1 * | 12/2015 | Shippert ................ | A61M 1/84 |
| | | | | 604/542 |
| 2019/0185814 | A1 * | 6/2019 | Bachrach ............ | A61L 27/3604 |

FOREIGN PATENT DOCUMENTS

| | | | | |
|---|---|---|---|---|
| WO | WO-2015/131087 | A1 | 9/2015 | |
| WO | WO-2019012337 | A1 * | 1/2019 | .............. A61M 1/79 |

* cited by examiner

FLEXIBLE BAG FOR THE PREPARATION OF ADIPOSE TISSUE GRAFTS AND RELATIVE KIT

CROSS-REFERENCE TO RELATED APPLICATIONS

This patent application is a U.S. national phase of International Patent Application No. PCT/IB2021/055404 filed Jun. 18, 2021, which claims the benefit of priority from Italian patent application no. 102020000014728 filed on Jun. 19, 2020, the respective disclosures of which are each incorporated herein by reference in their entireties.

TECHNICAL FIELD

The present invention concerns a flexible bag for the preparation of adipose tissue grafts and a relative kit.

PRIOR ART

In a clinical setting (for example in orthopaedic, plastic or reconstructive surgery applications) clinical treatments in which autologous adipose tissue is used have been known for some time. In particular, in these clinical treatments adipose tissue is removed from an area of the patient's body (for example by means of liposuction), it is micro-fragmented and filtered to separate it from proinflammatory oils and blood residues, and lastly the treated adipose tissue graft is implanted in another area of said patient's body for medical and/or aesthetic purposes.

During preparation of the grafts the adipose tissue removed (also called lipoaspirate) is micro-fragmented and subsequently separated into micro-fragmented adipose tissue rich in mesenchymal stem cells (called MSC which are multipotent cells with high regenerative capacity) and waste material which includes, for example, red blood cells, debris and inflammatory agents.

Currently the graft can be prepared in one of the following ways: by enzymatic treatment, the use of a centrifuge, or manually. Enzymatic treatment entails considerable handling of the adipose tissue with reduction of the multipotent capacity of the mesenchymal stem cells.

Preparation of the adipose tissue grafts by centrifugation is described, for example, by the document CN207659440. In particular, this document describes a device for centrifugation of the adipose tissue which comprises a rigid cylinder closed at the bottom by a base wall and at the top by a removable cover. The rigid cylinder houses a rotating shaft which has an axis substantially parallel to the axis of symmetry of the rigid cylinder and is provided with a plurality of filters which are equally spaced from one another defining several separation chambers arranged in succession one above the other. The rotating shaft and consequently the filters are rotated by a motor. During rotation of the filters the adipose tissue is centrifuged, washed by means of saline solution and filtered. The use of the centrifuge entails longer process times, is typically more costly because it requires the use of special machinery which must be positioned in dedicated locations and has non-negligible overall dimensions. Therefore, in recent times manual preparation of the graft has been preferred which can be carried out in any location, with single-use devices which are less costly and allow micro-handling, ensuring greater preservation of the original tissue structure. Furthermore, manual preparation of the graft allows the operator to perform quickly and safely the micro-fragmentation and extraction of the adipose tissue rich in regenerative and mesenchymal stem cells for re-grafting in the body of the patient from whom the non-treated adipose tissue has been removed.

Typically, manual preparation entails the use of a flexible bag such as, for example, the one described in the document WO2015131087, into which the non-treated adipose tissue is introduced and pushed, typically by means of a spatula, to move in the flexible bag, so as to be micro-fragmented and filtered.

The flexible bag of a known type is made of a front layer and a rear layer which are connected to each other by welding. Porous and flat filters are arranged in the flexible bag, each of the filters having dimensions (height and width) equal to the dimensions (height and width) of the flexible bag. The two layers and the two filters are welded together on all four sides and are all four substantially parallel to one another.

The above-mentioned bag for manual preparation of the graft has a plurality of drawbacks. Firstly, given its shape, the known bag tends to collapse, causing the two filters to adhere to each other due to the vacuum created during the treatment for preparation of the graft, requiring the aid of internal spacers to be inserted between the two filters, making production and management of the flexible bag more complicated. Furthermore, the filter with greater porosity tends to clog, effectively preventing passage of the filtered material through it. Therefore, the flexible bag of a known type, given the same lipidic material, allows a limited quantity of adipose tissue to be obtained.

In addition, the shape of the bag of a known type allows one single washing with saline solution to be carried out, effectively preventing further washing, emulsion and rinsing of the material during preparation.

In addition to this, the bags of a known type do not define, inside them, an obligatory path for the adipose tissue.

Lastly, due to the structure of the bag of a known type, there are various areas where non-treatable material stagnates (for example in the corners of the bag).

In other words, given the configuration of the bag and the arrangement of the openings for withdrawal of the graft and the waste, it is not possible to withdraw and completely remove the adipose tissue graft obtained.

DISCLOSURE OF THE INVENTION

The object of the present invention is, therefore, to provide a flexible bag for the preparation of adipose tissue grafts and a relative kit which are without the drawbacks of the state of the art and which are easy and inexpensive to produce.

According to the present invention the flexible bag for the preparation of adipose tissue grafts and the relative kit are provided as claimed in the attached claims.

BRIEF DESCRIPTION OF THE DRAWINGS

For a better understanding of the invention embodiments are described, purely by way of example, wherein.

PREFERRED EMBODIMENTS OF THE INVENTION

Figure 1:
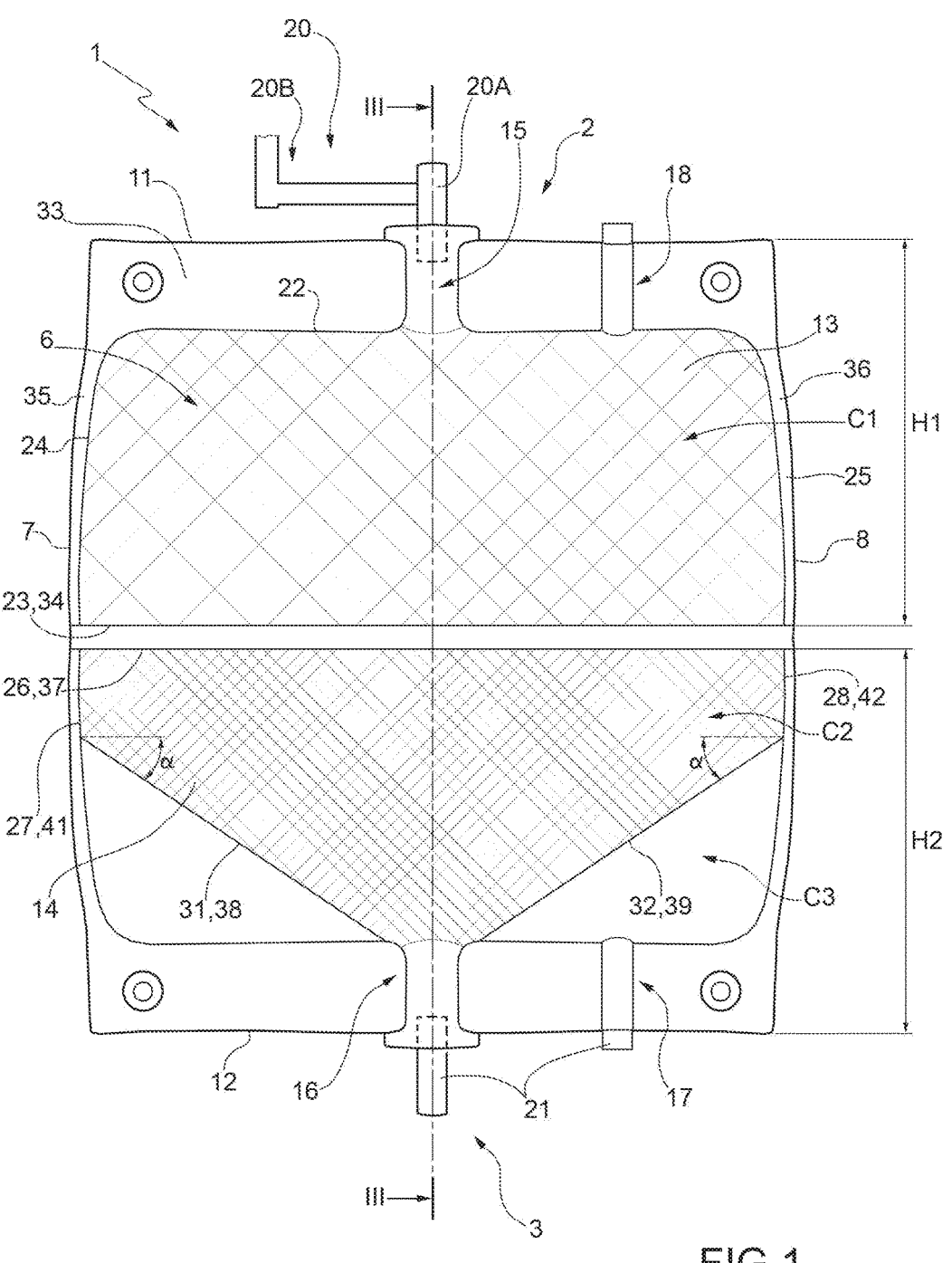
FIG. 1 is a plan view of the flexible bag for preparation of the grafts according to a first embodiment and in accordance with the present invention.

In FIG. 1 the number 1 indicates overall a flexible bag for the preparation of grafts I of autologous adipose tissue. Below, the graft I of adipose tissue will be indicated only as graft I.

The bag 1 allows micro-fragmentation of a non-treated adipose tissue TAN and separation of the graft I (desired part to be re-grafted) from a waste material MS (undesired part to be eliminated). The graft I comprises a large number of mesenchymal stem cells.

The waste material MS comprises red blood cells, debris and inflammatory agents.

The bag 1 is provided with a proximal end 2 and a distal end 3 which are opposite each other. As will be better described below, the non-treated adipose tissue TAN is introduced into the bag 1 preferably at the proximal end 2, whereas the graft I (i.e., the micro-fragmented and filtered adipose tissue) and the waste material MS are withdrawn from respective openings preferably at the distal end 3. Given the orientation illustrated in FIGS. 1 and 2, the proximal end 2 is arranged at the top, whereas the distal end 3 is arranged at the bottom.

According to a possible variation, not illustrated, at least one element selected from the non-treated adipose tissue TAN, the graft I and the waste material MS is introduced into the bag 1 or withdrawn from the bag 1 in a position between the proximal end 2 and the distal end 3.

Figure 2:
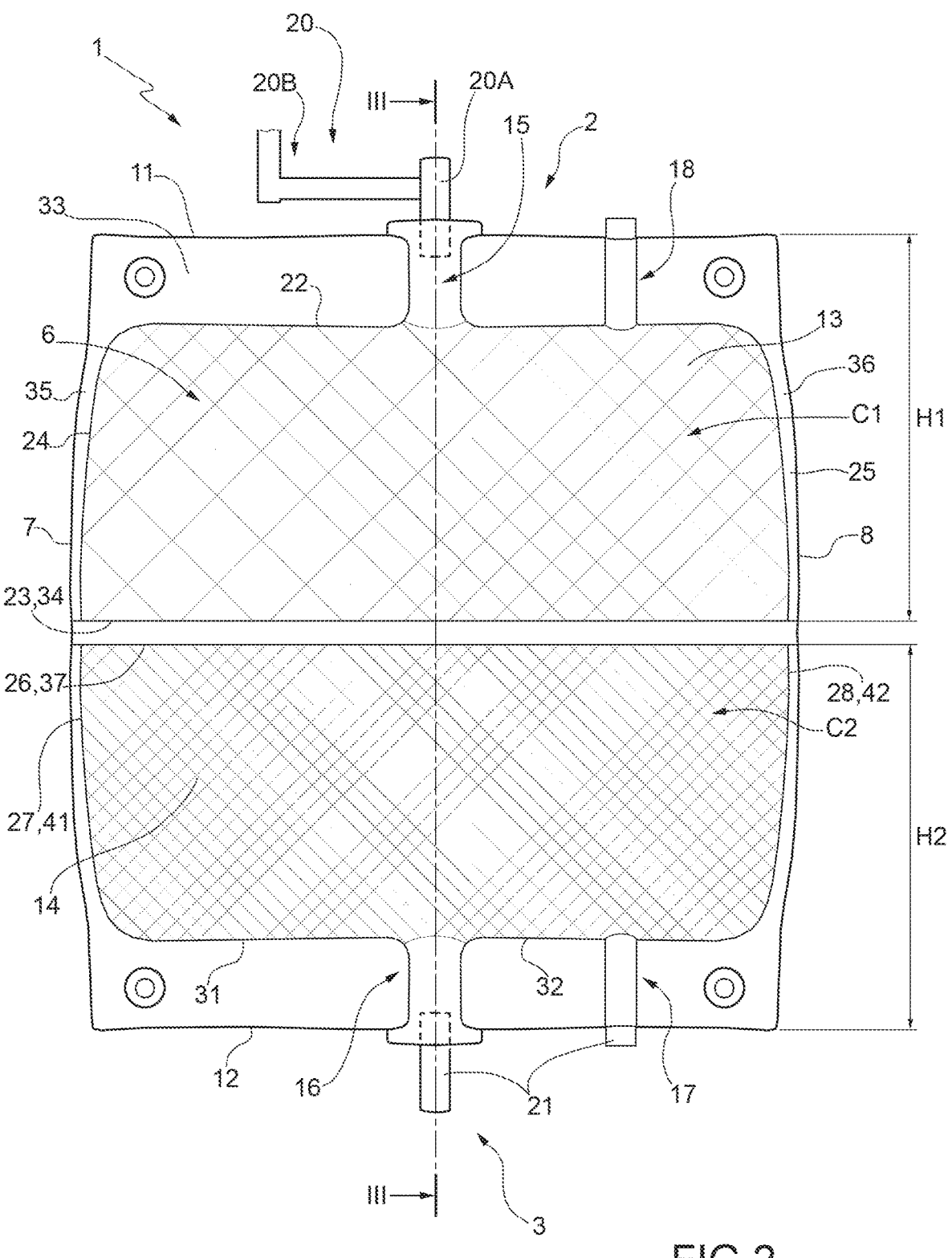
FIG. 2 is a plan view of the flexible bag for preparation of the grafts according to a second and alternative embodiment.
Figure 3:
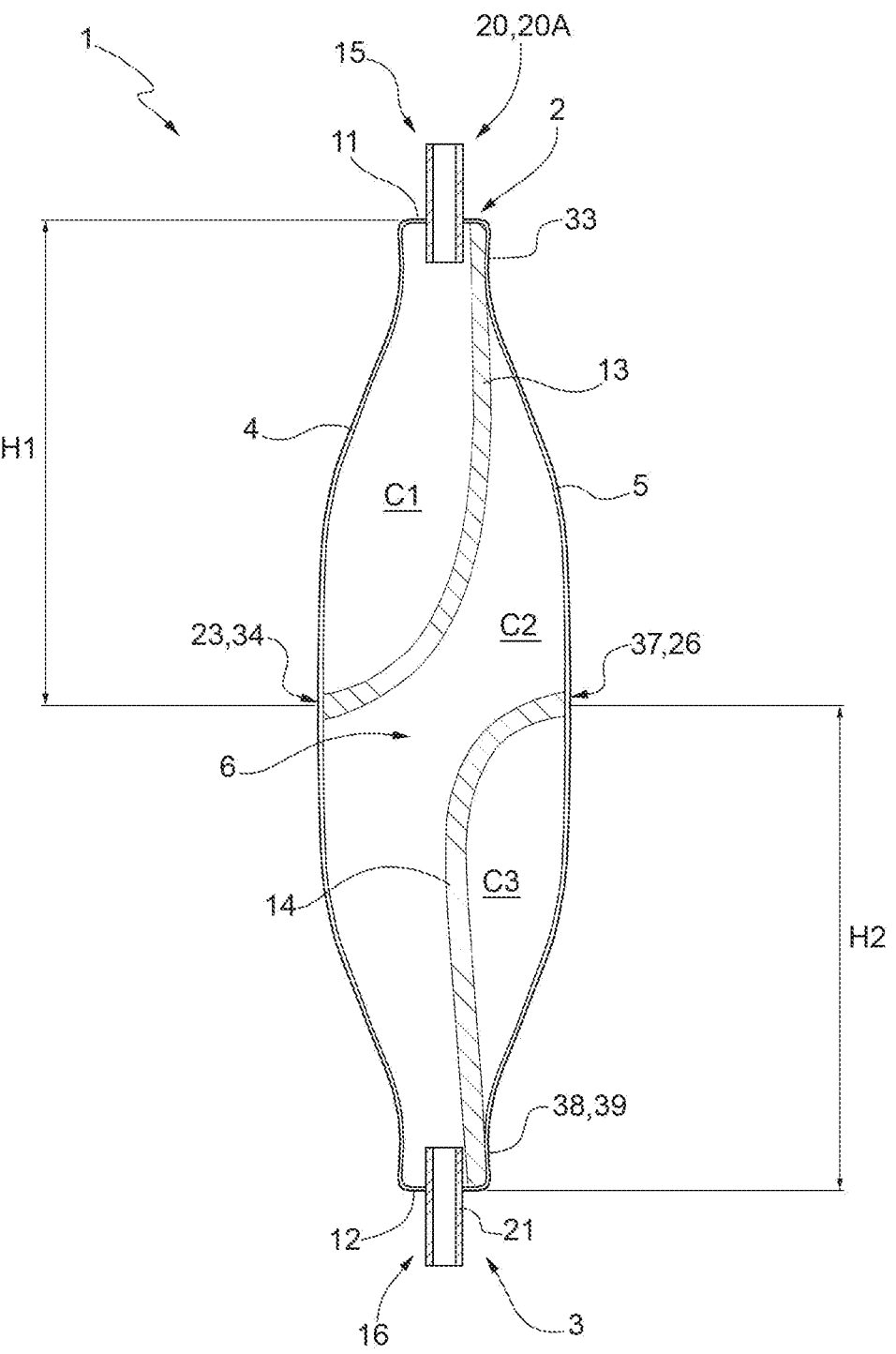
FIG. 3 is a sectional view along the line III-III of FIG. 1 and FIG. 2.

As can be seen from FIGS. 1-3, the bag 1 has a front wall 4 and a rear wall 5 which are flexible and each of which comprises two lateral edges 7 and 8, a proximal edge 11 and a distal edge 12. The edges 7, 8, 11 and 12 are connected to one another and delimit a receiving space 6 of the bag 1.

The bag 1 is a substantially flat element, namely it has its main extension in the plane parallel to the walls 4 and 5. Therefore, the bag 1 has a much smaller thickness (namely, the dimension measured in a direction orthogonal to the walls 4 and 5) than the dimension in plan view of the walls 4 and 5. FIG. 3 shows the thickness with enlarged dimension so as to facilitate understanding of the arrangement of the internal filters 13 and 14.

According to what is illustrated in FIGS. 1 and 2, the bag 1 has a substantially rectangular shape in plan view.

The receiving space 6 of the bag 1 is divided into three chambers C1, C2, C3 which are separated from one another by two filters 13 and 14. In other words, the chambers C1, C2 and C3 are interconnected and communicate with one another only through the filters 13 and 14. The filter 13 is arranged inside the bag 1 to divide the receiving space 6 into the chamber C1 and chamber C2. The filter 14 is arranged inside the chamber C2 to separate (namely, to obtain) the chamber C3. In FIG. 2 the chamber C3 is not visible since it is arranged behind chamber C2.

In particular, the filter 13 (also called separator) carries out micro-fragmentation of the non-treated adipose tissue TAN (namely, the adipose tissue TA which is taken from the patient), which is therefore activated.

In other words, the non-treated adipose tissue TAN as it passes through the filter 13 is dimensionally reduced, namely broken up into small pieces, obtaining the micro-fragmented adipose tissue TAF which has a grain size equal to or smaller than a porosity P1 of the filter 13. The filter 14 which has a porosity P2, lower than the porosity P1, separates the waste material MS from the micro-fragmented adipose tissue TAF, obtaining the graft I.

Advantageously, the filter 13 has porosity P1 ranging from 400 to 4000 μm, preferably from 750 to 1250 μm, in particular equal to approximately 1000 μm. The filter 14 has porosity P2 ranging from 25 to 100 μm, preferably from 45 to 55 μm, in particular equal to approximately 50 μm.

As illustrated in the embodiments of FIGS. 1-3, the bag 1 comprises four through openings 15, 16, 17 and 18. The openings 15 and 16 are arranged centrally, while the openings 17 and 18 are positioned laterally with respect to the openings 15 and 16. Through the opening 15 the non-treated adipose tissue TAN is fed into the bag 1 (at the chamber C1). Through the opening 16 the graft I is taken from the chamber C2. Through the opening 17 the waste material MS (separated from the graft I by the filter 14) is removed from the chamber C3. The opening 18 defines the air vent and allows the air inside the bag 1 to flow out independently during preparation of the graft I.

Advantageously, as illustrated in the attached figures, the opening 15 and the vent 18 are arranged at the proximal end 2. The openings 16 and 17 are arranged at the distal end 3.

According to a possible variation, not illustrated, at least one opening selected from the openings 15, 16, 17 and 18 is arranged between the proximal end 2 and the distal end 3. In particular, at least one opening selected from the openings 15, 16, 17 and 18 is arranged at the lateral edge 7 and/or 8 of the flexible bag 1.

Advantageously, in the opening 15 a forked connection duct 20 is inserted. The duct 20 comprises a central portion 20A through which the non-treated adipose tissue TAN is fed and a peripheral portion 20B, substantially "L" shaped, through which the saline solution is fed.

Similarly, a connection duct 21 is inserted also in the openings 16 and 17.

Advantageously, in the duct 20 of the opening 15 (in particular, in the portion 20A and in the portion 20B) and in the duct 21 of the opening 16 a valve is arranged (not illustrated) configured to allow or prevent passage of the material. Preferably, the valve is a Luer Lock type valve.

According to a first embodiment illustrated in FIG. 1, the filter 13 has a substantially rectangular shape in plan view with a proximal edge 22, a distal edge 23 and two lateral edges 24 and 25, whereas the filter 14 has an irregular pentagonal shape. In particular the filter 14 has in plan view the shape of a rectangular pentagon consisting of a rectangle below which, at a long side thereof, a triangle is arranged. The filter 14 has a proximal edge 26, two lateral edges 27 and 28 and two distal edges 31 and 32. The two lateral edges 27 and 28 are substantially transverse, in particular orthogonal, to the proximal edge 26, whereas each distal edge 31 or 32 is inclined by an angle α relative to an imaginary horizontal line. Therefore, as can be seen in FIG. 1, the two distal edges 31 and 32 form substantially a "V" shape which defines a funnel to facilitate feeding of the graft I towards the opening 16.

Advantageously, the angle α ranges from 30° to 60°, preferably from 40° to 50°.

According to a second embodiment illustrated in FIG. 2, both the filter 13 and the filter 14 have a substantially rectangular shape in plan view. Therefore, the filter 13 has a proximal edge 22, a distal edge 23 and two lateral edges 24 and 25 (as in FIG. 1), whereas the filter 14 has a proximal edge 26, two lateral edges 27 and 28 and one single distal edge 31 which is parallel to the proximal edge 22. The two lateral edges 27 and 28 are substantially transverse, in particular orthogonal, to the proximal edge 26 and to the distal edge 31.

According to a possible alternative embodiment (not illustrated), the filter 13 has a substantially rectangular shape in plan view (as in FIGS. 1 and 2), whereas the filter 14 has a triangular shape in plan view. Therefore, in this case the filter 14 has only the proximal edge 26 and the two distal edges 31 and 32. In other words, compared to FIG. 1 the lateral edges 27 and 28 are absent. Each distal edge 31 or 32 is inclined with respect to the imaginary horizontal line of the above-mentioned angle α.

Figure 5:
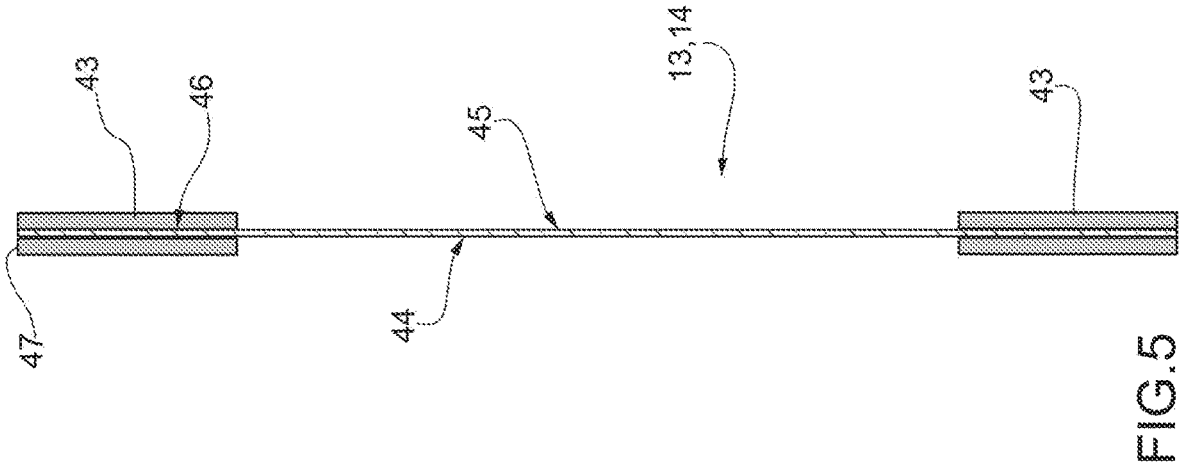
FIG. 5 is an enlarged sectional view along the line V-V of FIG. 4.
Figure 4:
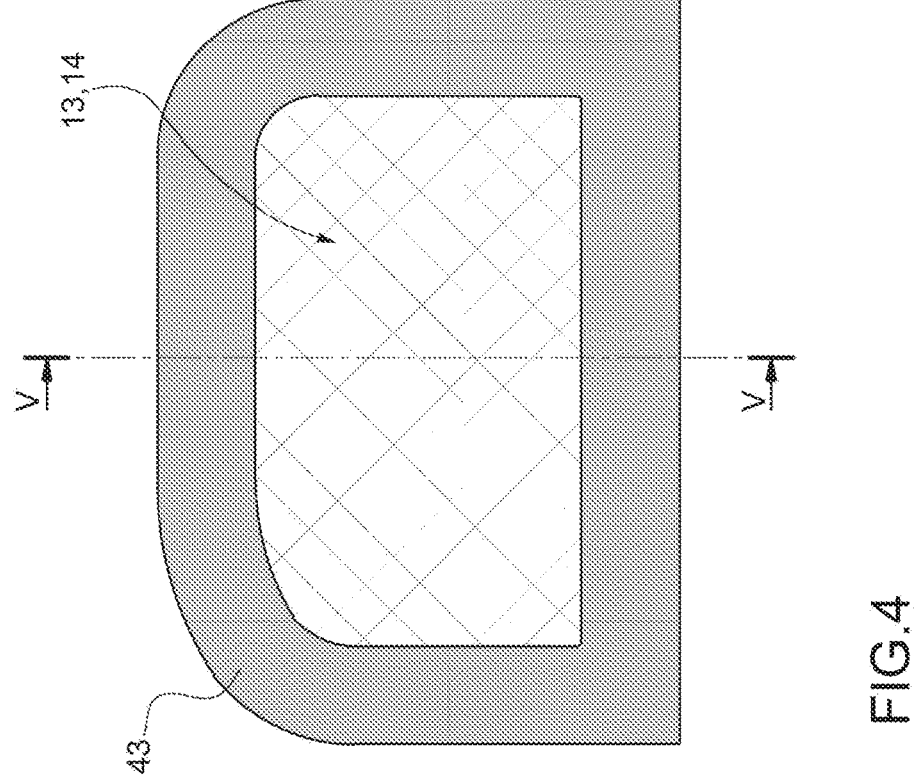
FIG. 4 is a plan view of a possible embodiment of a filter of the flexible bag of FIG. 1 or 2.

According to a possible variation, the filter 13 and/or the filter 14 comprises a frame 43 (illustrated schematically in grey in FIGS. 4 and 5). In other words, one of the filters 13 or 14 or both the filters 13 and 14 are provided with a respective frame 43 connected thereto. In particular, the frame 43 is arranged around the respective filter 13 or 14.

The frame 43 is made of a flexible and preferably non-filtering material. The frame 43 preferably has a smooth surface, namely without partitions or ribs protruding from it.

According to a possible variation, the filter 13 and/or 14 has a single frame 43. In other words, the frame 43 is applied at a single front surface 44 or a rear surface 45 (which is opposite the front surface 44) of the respective filter 13 or 14. Alternatively, the filter 13 and/or 14 has a double frame 43 (as illustrated schematically in FIG. 5), namely it is arranged in the area both of the front surface 44 and the rear surface 45 of the respective filter 13 or 14.

Preferably, the thickness of the frame 43 is less than or equal to the thickness of the remaining portion of the filter 13 or 14. Alternatively, as illustrated schematically in FIG. 5, the thickness of the frame 43 can be greater than the thickness of the remaining portion of filter 13 or 14.

Advantageously, if the filter 13 or 14 has the frame 43, at least one peripheral overlapping portion 46 can be present in which the frame 43 is connected to the filter 13 or 14.

Alternatively, even if the filter 13 or 14 is provided with the frame 43, the peripheral portion can be absent (namely, the filter is without the peripheral portion). In this case the connection between the frame 43 and the respective filter 13 or 14 is not made by overlapping said elements, but can be made for example by means of the head connection.

Advantageously, the frame 43 has an own outer edge 47 which can protrude beyond the outer edge (namely the proximal and/or distal edge and/or lateral edge) of the respective filter 13 or 14. In this case, the frame 43 increases the dimension in plan view of the filter 13 or 14. Alternatively, as illustrated schematically in FIG. 5, the outer edge 47 can be substantially aligned with the outer edge (namely the proximal edge and/or the distal edge and/or lateral edge) of the respective filter 13 or 14. In this case, the frame 43 does not increase the dimension in plan view of the filter 13 or 14.

Advantageously, the frame 43 has the outer edge 47 that defines the geometric shape of the respective filter 13 or 14. In the following discussion, explicit reference will be made to the proximal edges 22 and 26, the distal edges 23, 31, 32 and the lateral edges 24, 25, 27, 28 of the filters 13 and 14, independently of whether the frame 43 is present or not. Namely, since the frame 43 forms part of the respective filter 13 or 14, the following description must be understood to refer also to the outer edges 47 of the frame 43 (if present). In other words, what is described for the proximal edges 22 and 26, the distal edges 23, 31, 32 and the lateral edges 24, 25, 27, 28 of the filters 13 and 14 is understood to be described also for the respective proximal, distal and lateral edges of the respective filters 13 and 14 in the presence of the frame 43. Obviously in this case the filter 13 and/or 14 provided with the frame 43 will be connected to the front wall 4 and/or to the rear wall 5 at the frame 43 thereof.

Summarizing, in all the embodiments, the bag 1 has the filter 13 that comprises the distal edge 23 which is connected to the front wall 4 between the proximal end 2 and the distal end 3 of the bag 1 (namely, in an intermediate position between the two ends 2 and 3) and the filter 14 that comprises the proximal edge 26 which is connected to the rear wall 5 between the proximal end 2 and the distal end 3 of the bag 1 (namely, in an intermediate position between the two ends 2 and 3).

As illustrated in FIGS. 1-3, the proximal edge 22 of the filter 13 is connected to the proximal end 2 by means of a transverse joining line 33. The distal edge 23 is connected to the front wall 4 by means of another transverse joining line 34. The two lateral edges 24 and 25 are, on the other hand, connected to the lateral edges 7 and 8 of the front wall 4 and the rear wall 5 respectively, by means of a respective longitudinal joining line 35 and 36.

In the first embodiment of FIG. 1, in which the filter 14 has a pentagonal shape in plan view, the proximal edge 26 is connected to the rear wall 5 by means of a transverse joining line 37 and the two distal edges 31 and 32 are connected to the rear wall 5 and to the distal end 3 by means of two angled joining lines 38 and 39. The two lateral edges 27 and 28 are, on the other hand, connected to the lateral edges 7 and 8 of the front wall 4 and the rear wall 5 respectively by means of a respective longitudinal joining line 41 and 42. In this embodiment, the transverse joining lines 33, 34 and 37 of the filters 13 and 14 are substantially parallel to one another and extend substantially in a horizontal direction, whereas the angled joining lines 38 and 39 are arranged substantially in a "V" shape and are inclined by the angle α. The two joining lines 38 and 39 therefore converge towards the opening 16 to facilitate the descent of the micro-fragmented adipose tissue TAF and subsequent withdrawal of the graft I.

In the second embodiment of FIG. 2, in which the filter 14 has a rectangular shape in plan view, the proximal edge 26 is connected to the rear wall 5 by means of the transverse joining line 37, the edge 31 is connected to the rear wall 5 and to the distal end 3 by means of the transverse joining line 38 and the two lateral edges 27 and 28 are connected to the lateral edges 7 and 8 of the front wall 4 and the rear wall 5 respectively by means of the respective longitudinal joining line 41 and 42. According to this embodiment the transverse joining lines 37 and 38 are transverse, preferably orthogonal, to the longitudinal joining lines 41 and 42. In this embodiment, the transverse joining lines 33, 34, 37 and 38 of the filters 13 and 14 are substantially parallel to one another and extend substantially in a horizontal direction.

In the embodiment not illustrated, in which the filter 14 has a triangular shape in plan view, the proximal edge 26 is connected to the rear wall 5 by means of the transverse joining line 37 and the two distal edges 31 and 32 are connected to the rear wall 5 and to the distal end 3 by means of two angled joining lines 38 and 39. In this embodiment, the transverse joining lines 33, 34 and 37 of the filters 13 and 14 are substantially parallel to one another and extend substantially in a horizontal direction, whereas the angled joining lines 38 and 39 are arranged substantially in a "V" shape and are inclined by the angle α. The two joining lines 38 and 39 therefore converge towards the opening 16 to facilitate the descent of the micro-fragmented adipose tissue TAF and subsequent withdrawal of the graft I.

Advantageously, in the first and second embodiments discussed above, the joining lines 35 and 41, like the joining lines 36 and 42, can be connected to each other forming respectively one single joining line 35 or 36. It is understood that the lines 33, 35, 36, 41 (if present) and 42 (if present) can be defined by the same joining lines that connect the front wall 4 to the rear wall 5.

As illustrated in the sectional view of FIG. 3 (which is the sectional view of both FIG. 1 and FIG. 2), the filter 13 is connected to an intermediate portion of the front wall 4 and is connected to the rear wall 5 only at the proximal end 2, whereas the filter 14 is connected to the rear wall 5 at an intermediate portion and the distal end 3.

Advantageously, the distal edge 23 of the filter 13 is connected to the intermediate portion of the front wall 4 at a distance H1 from the proximal end 2. The distance H1 is therefore the dimension measured parallel to the direction of longitudinal extension of the bag 1 between the connection point of the distal edge 23 of the filter 13 to the front wall 4 and the proximal end 2, whereas the proximal edge 26 of the filter 14 is connected to the intermediate portion of the rear wall 5 at a distance H2 from the distal end 3. The distance H2 is therefore the dimension measured parallel to the direction of longitudinal extension of the bag 1 between the connection point of the proximal edge 26 of the filter 14 to the rear wall 5 and the distal end 3.

Advantageously, the distances H1 and H2 are approximately equal.

Alternatively, to modulate the dimension of the chambers C1, C2 and C3 the distance H1 could be greater or smaller than the distance H2.

Advantageously, the joining lines 33-42 are produced by means of gluing or welding (in particular ultrasound or dielectric welding).

Advantageously, the walls 4 and 5 are made of plastic material such as, for example, Polyurethane or Evatane, whereas the filters 13 and 14 are made of Polyester. The frame 43 (if present) is made of a plastic material such as, for example, Polyurethane or Evatane.

The present invention also comprises a kit (not illustrated) for preparation of the grafts I. The kit comprises at least the bag 1 and a spatula (not illustrated) for handling the adipose tissue present inside the chambers C1, C2 and C3 of the bag 1. In addition, the kit can also comprise a rigid closed housing inside which the bag 1 is inserted during preparation of the graft I. The housing has a front opening through which it is possible to operate the spatula for handling the adipose tissue TA in the bag 1.

In use, the operator feeds to the bag 1 through the opening 15 the non-treated adipose tissue TAN (in particular by means of the portion 20A) and the saline solution (in particular by means of the portion 20B). At this point, the operator begins to move the adipose tissue TA by means of the spatula inside the bag 1. In particular, the operator will carry out a plurality of movements of the spatula in the direction of greatest extension of the bag 1 and in the directions transverse to it. In other words, considering the orientation of the bag 1 illustrated in the attached figures, the operator will move the spatula several times (namely by several spatula passes) on the wall 4 or 5 of the bag 1. In this way, the entire quantity of the non-treated adipose tissue TAN is obliged to pass through the filter 13 to micro-fragment it and by continuing to move the spatula, the operator ensures that all the waste material MS is separated by the filter 14, therefore passing from the chamber C2 to the chamber C3. Once the chamber C1 is substantially empty and the operator considers that all the micro-fragmented tissue TAF present in the chamber C2 has been filtered by the filter 14, he can proceed with elimination of the waste material MS through the opening 17 and can withdraw the graft I from the opening 16. The graft I therefore has a grain size (namely, a dimension) between the porosity P1 of the filter 13 and the porosity P2 of the filter 14.

It is understood that elimination of the waste material MS and/or withdrawal of the graft I can also take place at least partially during an intermediate phase of preparation of the graft I, namely between the various spatula passes.

The bag 1 and the kit described so far have a plurality of advantages.

Firstly, with the same amount of non-treated adipose tissue TAN placed in the bag 1, it is possible to obtain a larger quantity of graft I.

The shape of the bag 1 defines an obligatory path of the adipose tissue TA inside said bag 1, said tissue being forced to pass through the filter 13 where it is micro-fragmented and through the filter 14 where it is filtered.

The bag 1 comprising the filter 14 having substantially pentagonal or triangular shape allows for reduction or even avoidance of stagnation areas of the adipose tissue TA (both the micro-fragmented tissue TAF not yet filtered and the filtered adipose tissue—namely the graft I).

The bag 1 allows for continuous washing, emulsion and rinsing with saline solution throughout preparation of the graft I in the bag 1.

In this way it is possible to obtain a graft I with multi-potent cells with high regeneration capacity and a lower percentage of proinflammatory factors (namely, the waste material MS). In addition, the adipose tissue TA apart from being washed is also activated, releasing molecules that facilitate the subsequent re-implant. Due to the continuous washing, any parts of material clogging the filter 13 and/or 14 are removed.

In addition, the bag 1 subject of the present invention cannot collapse. In other words, given the arrangement of the filters 13 and 14 they cannot adhere to each other during preparation of the graft in the bag 1.

The invention claimed is:

1. A flexible bag for the preparation of an adipose tissue graft from adipose tissue (TA)

(I), which is provided with a proximal end and with a distal end and comprising:

(a) a flexible, front wall and a flexible, rear wall, which are connected to one another so as to define a receiving space on the inside;

(b) a first filter, which is arranged inside the bag so as to divide the receiving space into a first chamber (C1) and a second chamber (C2); the first filter is configured to micro-fragment a non-treated adipose tissue (TAN) to obtain a micro-fragmented adipose tissue (TAF); and (c) a second filter arranged inside the second chamber (C2) so as to obtain a third chamber (C3); the second filter is configured to obtain the graft (I) by separating a waste material (MS) from the micro-fragmented adipose tissue (TAF);

wherein the first filter comprises a distal edge which is connected to the flexible, front wall between the proximal end and the distal end; and the second filter comprises a proximal edge which is connected to the flexible, rear wall between the proximal end and the distal end whereby the first filter and the second filter are spaced-apart from each other thereby inhibiting adherence of the first filter and the second filter to each other and collapse of the flexible bag during external deformation of the flexible bag pushing the adipose tissue through the flexible bag from the first filter to the second filter, wherein the first filter and the second filter are spaced-apart from each other along a longitudinal direction of the flexible bag.

2. The bag according to claim 1, further comprising a first through opening to feed the non-treated adipose tissue (TAN) into the first chamber (C1), a second through opening to withdraw the graft (I) from the second chamber (C2) and a third through opening to remove the waste material (MS) from the third chamber (C3).

3. The bag according to claim 2, wherein the first opening is arranged at the proximal end and wherein the second opening and the third opening are arranged at the distal end.

4. The bag according to claim 2, wherein at least an opening selected from the first opening, the second opening and the third opening is arranged between the proximal end and the distal end.

5. The bag according to claim 2, wherein in the first opening a forked connection duct is inserted that comprises a central portion through which the non-treated adipose tissue (TAN) is fed and a peripheral portion through which the saline solution is fed.

6. The bag according to claim 1, wherein the first filter has a rectangular shape in plan view and is connected to the proximal end and to the front wall; and the second filter has a rectangular shape in plan view and is connected to the distal end and to the rear wall.

7. The bag according to claim 1, wherein the first filter has a rectangular shape in plan view and is connected to the proximal end and to the flexible, front wall; and the second filter has a triangular or pentagonal shape in plan view and is connected to the distal end and to the flexible, rear wall; wherein the second filter has two distal edges which are inclined by an angle ($\alpha$) with respect to an imaginary horizontal line and the angle ($\alpha$) is between 30° and 60°.

8. The bag according to claim 7, wherein the two distal edges of the second filter are connected to the flexible, rear wall and to the distal end through two angled joining lines.

9. The bag according to claim 1, wherein the distal edge of the first filter is connected to the flexible, front wall at a first distance (H1) from the proximal end and the proximal edge of the second filter is connected to the flexible, rear wall at a second distance (H2) from the distal end.

10. The bag according to claim 9, wherein the first distance (H1) is approximately equal to the second distance (H2).

11. The bag according to claim 9, wherein the first distance (H1) is less than or greater than the second distance (H2).

12. The bag according to claim 1, wherein the first filter has a first porosity (P1) ranging from 400 to 4000 μm, and wherein the second filter has a second porosity (P2) ranging from 25 to 100 μm.

13. The bag according to claim 1, wherein the first filter and/or the second filter has a frame arranged around the respective filter.

14. The bag according to claim 13, wherein the frame is applied in the area of a front surface and/or a rear surface of the filter, the rear surface being opposite the front surface.

15. A kit for the preparation of adipose tissue grafts (I) comprising the bag according to claim 1 and a spatula for handling the adipose tissue housed inside the bag.

16. The bag according to claim 4, wherein the at least one opening is arranged at lateral edge of the bag.

17. The bag according to claim 8, wherein the two angled joining lines have an angle ($\alpha$), which converges towards the second opening.

18. The bag according to claim 12, wherein the first filter has a first porosity (P1) ranging from 750 to 1250 μm, and/or the second filter has a second porosity (P2) ranging from 25 to 100 μm.

19. The bag according to claim 12, wherein the first filter has a first porosity (P1) equal to 1000 μm.

20. The bag according to claim 12, wherein the second filter has a second porosity (P2) equal to 50 μm.

* * * * *